US007258675B2

(12) United States Patent
Nichols

(10) Patent No.: US 7,258,675 B2
(45) Date of Patent: Aug. 21, 2007

(54) FACIAL REJUVENATION DEVICE AND METHOD

(76) Inventor: Thomas Nichols, Pretika Corporation, North American Market Headquarters, 16 Salermo, Laguna Niguel, CA (US) 92677

(*) Notice: Subject to any disclaimer, the term of this patent is extended or adjusted under 35 U.S.C. 154(b) by 493 days.

(21) Appl. No.: 10/442,994

(22) Filed: May 21, 2003

(65) Prior Publication Data

US 2004/0236254 A1 Nov. 25, 2004

(51) Int. Cl.
*A61H 7/00* (2006.01)
*A61M 1/00* (2006.01)

(52) U.S. Cl. ............................ 601/10; 601/6; 604/315

(58) Field of Classification Search .................... 601/6, 601/7, 9, 10, 12–14, 17; 604/314, 316, 313, 604/315

See application file for complete search history.

(56) References Cited

U.S. PATENT DOCUMENTS 1,704,960 A * 3/1929 Ackerman ..................... 601/7
4,878,894 A * 11/1989 Sutter et al. .................. 604/24
5,003,966 A 4/1991 Saka et al. .................... 128/39
5,593,381 A * 1/1997 Tannenbaum et al. ........ 601/93
6,319,211 B1 11/2001 Ito et al. ........................ 601/7
6,468,235 B2 10/2002 Ito et al. ........................ 601/6
6,511,445 B2 * 1/2003 Sivan et al. ................... 601/6
2001/0041848 A1 11/2001 Ito et al.
2005/0119594 A1 * 6/2005 Piana et al. .................... 601/7

* cited by examiner

*Primary Examiner*—Danton D. DeMille
(74) *Attorney, Agent, or Firm*—Steins & Assocaites, P.C.

(57) ABSTRACT

An Improved Facial Rejuvenation Device and Method. The device is small and portable. The device further has an ergonomic nozzle shape defined by a housing having a suction bore defined by a throttle positioned within it. The throttle may perform its throttling action by adjusting the diameter of the suction bore formed within the housing. The method employs the unique device to create a localized suction force to the skin in the vicinity of a previously-applied medicinal formulation. The device further may have a housing defined by a conical outer shape terminating in a sealing ring at its tip.

6 Claims, 4 Drawing Sheets

FACIAL REJUVENATION DEVICE AND METHOD

BACKGROUND OF THE INVENTION

1. Field of the Invention

This invention relates generally to skin care and, more specifically, to an Improved Facial Rejuvenation Device and Method 2. Description of Related Art The skin care industry has undergone explosive growth in recent years. Daily, additional lotions, treatments and devices arrive on the market that are touted to reduce the effects of age and harsh environmental conditions on a person's skin. A somewhat recent approach has been to apply a localized vacuum source against a user's skin in order to remove the upper layer(s) of dead skin (the sebum) and other debris. A portable device now available for such application is provided in FIG. 1.

FIG. 1 is a perspective view of a conventional portable suction device 10. the device 10 is defined by a somewhat ergonomic handle 12, from which extends a head 14. The head 14 is defined by a neck 16 that tapers down in diameter to a rim 18. A suction port stem 20 extends from the head 14 in the center portion of the rim 18; the gap between the suction port stem 20 and the rim 18 being defined here as an annular ring 24. Near the distal end of the stem 20 is a gasket 22, such as a conventional "O" ring.

The handle 12 is defined by an "on-off" switch 26, and a removable cover 28 which encases the batteries used to power the electric motor contained within the device 10 for creating the suction. To operate the device 10, the user need simply turn on the switch 26; the motor will drive a small internal pump (not shown), which will create a vacuum at the opening in the suction port stem 20. The stem 20 is intended to permit the user to attach and detach a variety of brushes or tips for creating a suction against the user's (or patient's) skin.

There are at least two deficiencies with this prior device 10: (1) it fails to address the need for having adjustability in the level of vacuum being applied to the skin; and (2) it fails to provide an ergonomic tip attachment that can be used to massage the skin, rather than simply to remove dead or dying skin.

Ito I and Ito II, U.S. Pat. Nos. 6,319,211 and 6,468,235 both attempt to address the need for a variable vacuum source. The Ito devices both couple a battery-operated suction-developing device with a detachable nozzle (similar to FIG. 1 in their basic design); the alleged novelty in these devices is related to their ability to regulate the vacuum power. The Ito devices recite the addition of a "regulator" for regulating the pump characteristics such that the suction created by the pump can be varied. The purpose articulated for regulating the vacuum is to enable the device to be removed more easily from the user's face, and to thereby prevent the creation of purplish marks on the skin.

While the Ito's both disclose a device for regulating the suction created at the tips of the devices, neither does so in a manner that is cost-effective or ergonomic. Furthermore, the Ito disclosures fail to address the application of localized suction to the skin as a massaging technique that further prepares the dermis and subcutaneous tissue to improve the subcutaneous delivery of medicinal formulation. What is needed, therefore, is a device and method that modifies a conventional suction device such that the suction strength is adjustable and to provide an improved delivery system for topical applications of skin rejuvenating formulations.

SUMMARY OF THE INVENTION

In light of the aforementioned problems associated with the prior devices and methods, it is an object of the present invention to provide an Improved Facial Rejuvenation Device and Method. The device should be small and portable. The device should further have an ergonomic nozzle shape defined by a housing having a suction bore defined by a throttle positioned within it. The throttle may perform its throttling action by adjusting the diameter of the suction bore formed within the housing. The method should employ the unique device to create a localized suction force to the skin in the vicinity of a previously-applied medicinal formulation. The device may have a housing defined by a conical outer shape terminating in a sealing ring at its tip.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an Improved Facial Rejuvenation Device and Method.

Figure 1:
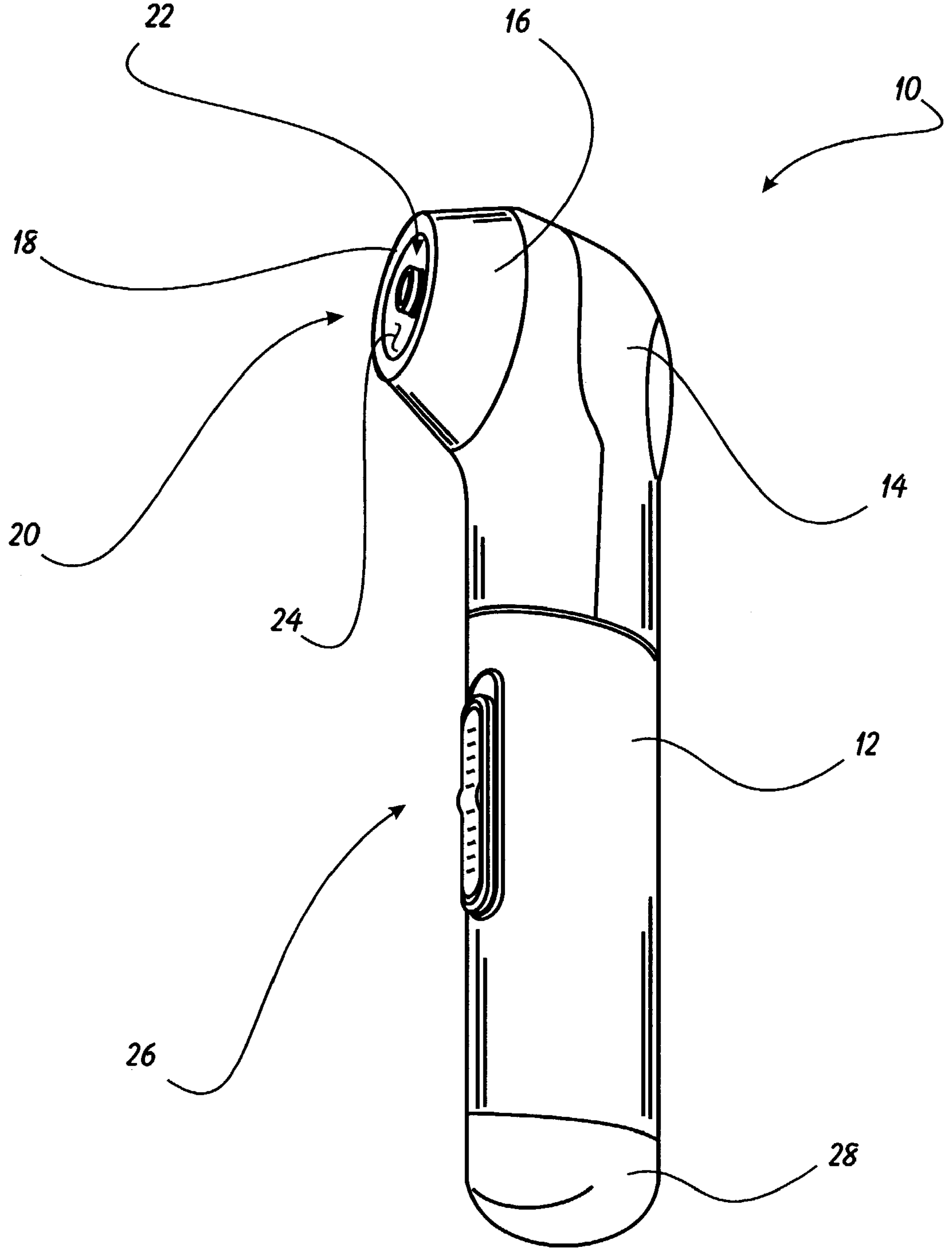
FIGURE 1 PRIOR ART
FIG. 1 is a perspective view of a conventional portable suction device.
Figure 2:
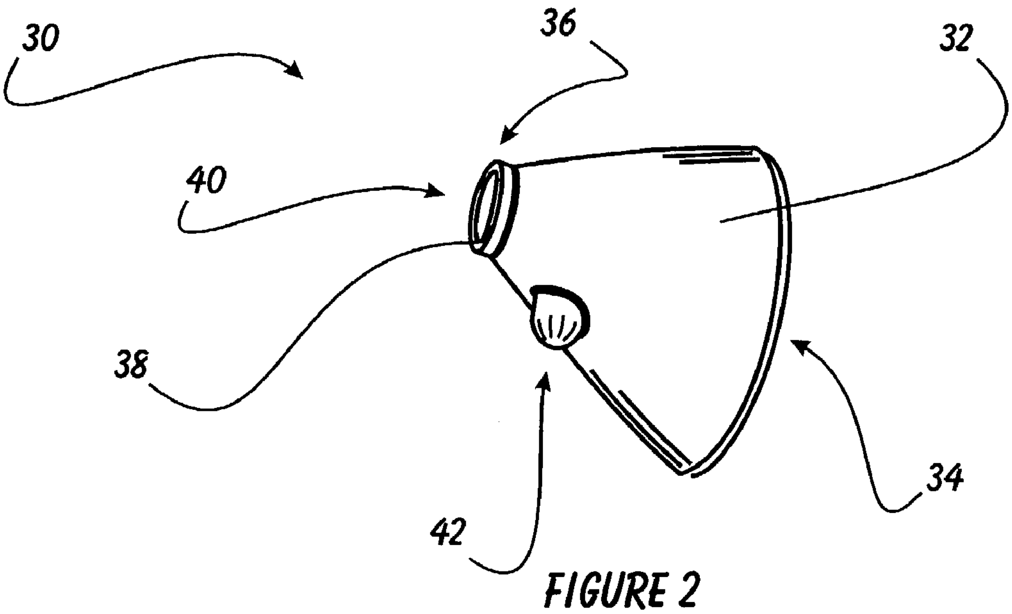
FIG. 2 is a front perspective view of the conical tip attachment of the present invention.

The present invention can best be understood by initial consideration of FIG. 2. FIG. 2 is a front perspective view of the conical tip attachment 30 of the present invention. The attachment 30 is configured to be detachably attached to a conventional suction-creating device, such as the one depicted above in FIG. 1, as well as other devices and systems. The attachment 30 is defied by a housing 32 having a conical outer shape. The conical shape of the housing 32 is an important distinction from the prior devices because it is less cumbersome to use, particularly in the facial area, and it is further more aesthetically pleasing. The housing 32 has a skirt edge 34 at the widened end of the cone shape, and is defined by the tip end 36 opposite. A sealing ring 38 is attached or formed at the tip end 36. the sealing ring 38 is made from a pliable material, such as silicone, rubber or plastic material. Substantially in the center of the sealing ring 38 is an aperture 40.

Disposed along the wall of the housing 32 is a throttle knob 42. As will be discussed more fully below, the throttle knob 42 is the interface for the user to increase or decrease the amount of suction being provided through the aperture 40. In this example, the housing 32 and throttle knob 42 are constructed from a rigid, durable material, such as molded plastic; other materials may be employed depending upon the particular application for the device 30. Now turning to FIG. 3, we can examine other aspects of the present invention.

Figure 3:
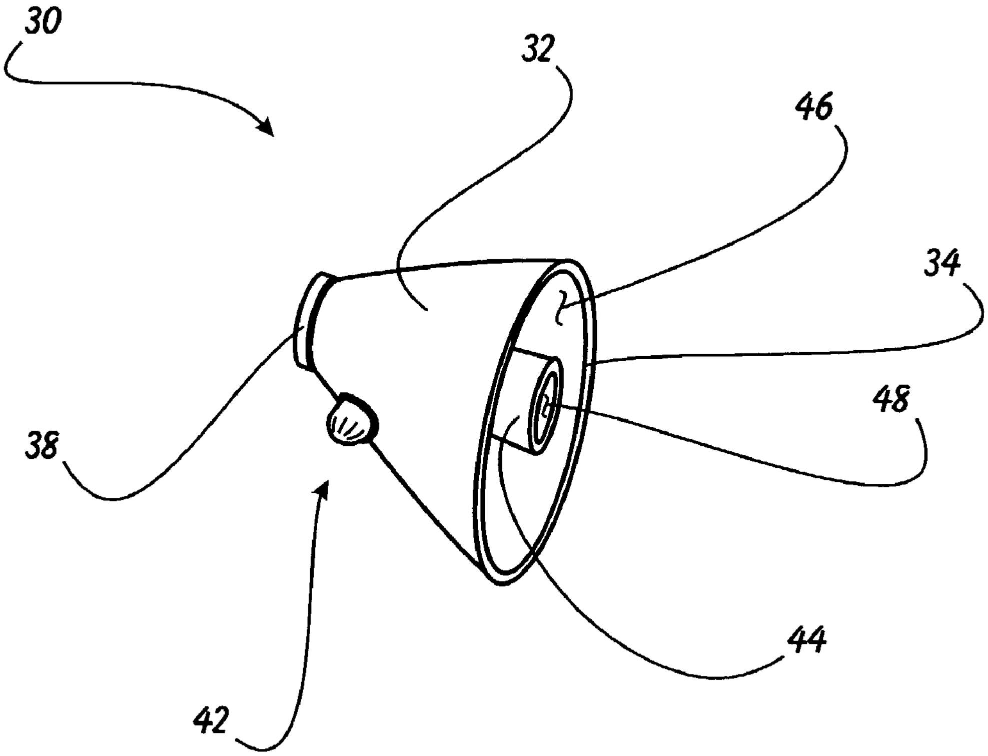
FIG. 3 is a rear perspective view of the attachment of FIG. 2.

FIG. 3 is a rear perspective view of the attachment 30 of FIG. 2. The attachment 30 has a suction interface tube 44 extending rearwardly from substantially the center of the skirt edge 34. The tube 44 defines a suction bore 48 at its center, and further an annular ring 46 between its exterior surface and the inner wall of the housing 32 commencing with the skirt edge 34.

Figure 4:
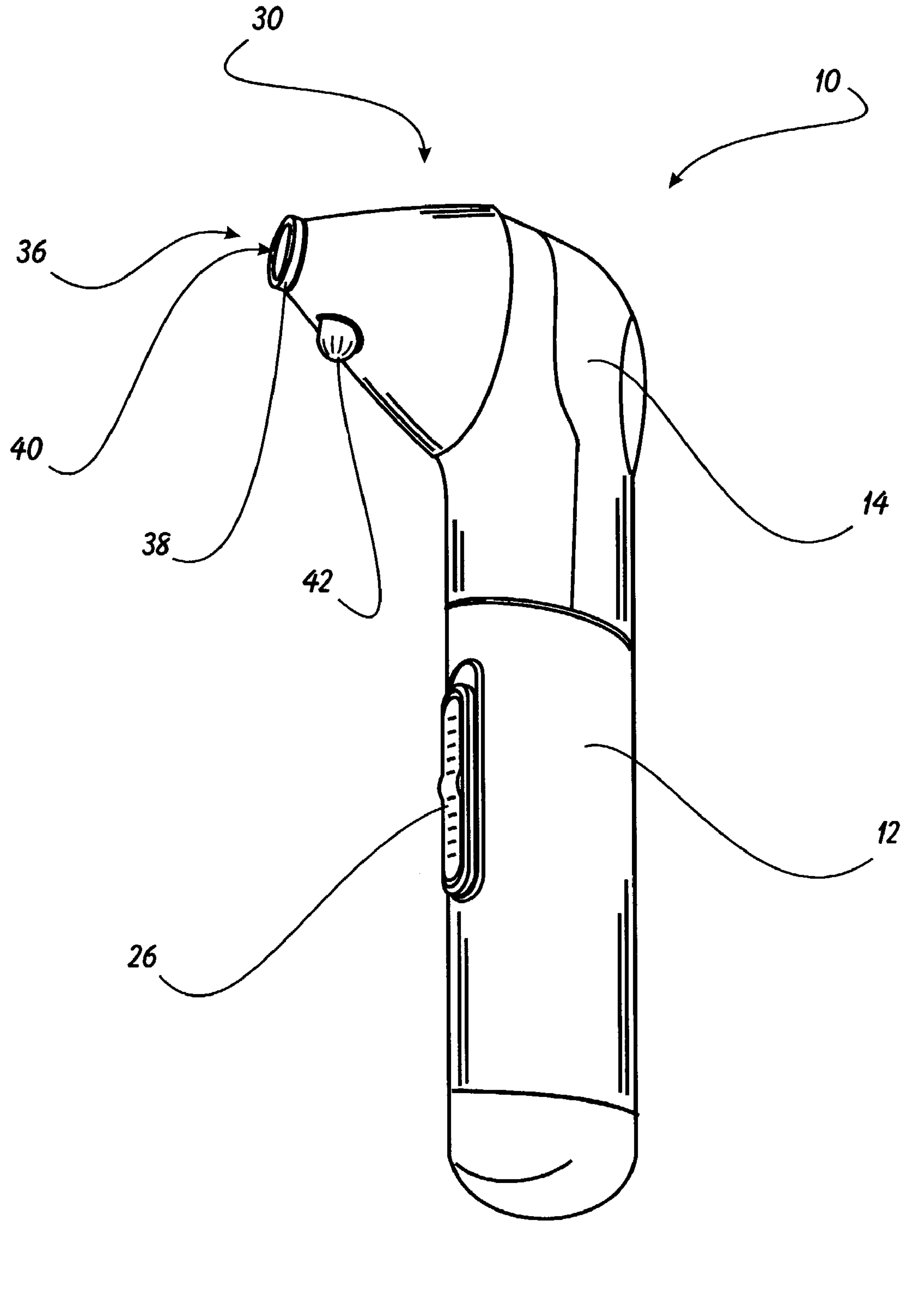
FIG. 4 is a perspective view of the attachment of FIGS. 2 and 3 attached to the device of FIG. 1.

The tube 44 is cooperatively designed to be placed over the suction port stem (see FIG. 1), and to create a leak-proof seal between the two. The rim of the suction device (see FIG. 1) will be accepted within the annular ring 46 of the attachment 30. Since the housing 32 and interface tube 44 have circular cross-sections, the attachment 30 can be rotated to any angular position desired; the user can thus position the throttle knob 42 on whichever side of the housing 32 that he or she finds convenient. FIG. 4 reflects the completed assembly.

FIG. 4 is a perspective view of the attachment 30 of FIGS. 2 and 3 attached to the device 10 of FIG. 1. As shown, the attachment 30 provides a very sleek, ergonomic addition to the conventional suction device 10. As discussed above, the attachment 30 can be rotated to position the throttle knob 42 as desired such that the suction force is conveniently adjusted.

It should be apparent that when the switch 26 is activated, it will cause the motor and pump to run, thereby causing a suction to be developed at the stem (see FIG. 1). This suction will in turn be created at the tip end 36 through the aperture 40. Once this suction is developed, the assembled device 10 and attachment 30 can be used to perform a unique process.

As discussed above in the background section, no prior device or method has been used to assist in the subcutaneous delivery of skin care lotions or creams. This device is designed to be gently passed over the user's skin, typically the facial area. The suction developed at the sealing ring 38 serves to stretch the skin as the attachment 30 is placed against a particular skin area. As the skin is stretched not only are the pores opened in the outer layer of the skin, but the circulation within the underlying tissue of the skin (i.e. the epidermis) is also increased. Furthermore, the collagen and elastin fibers that are found in the outer layer of skin are stretched; this creates additional elasticity in the skin. The additional skin elasticity will diminish the appearance of wrinkles, will reduce fine lines in the skin, and will generally improve overall skin tone. Still further, when the attachment 30 is used in conjunction with a topical collagen-enriched skin cream or lotion, even better results are achieved.

Figure 5:
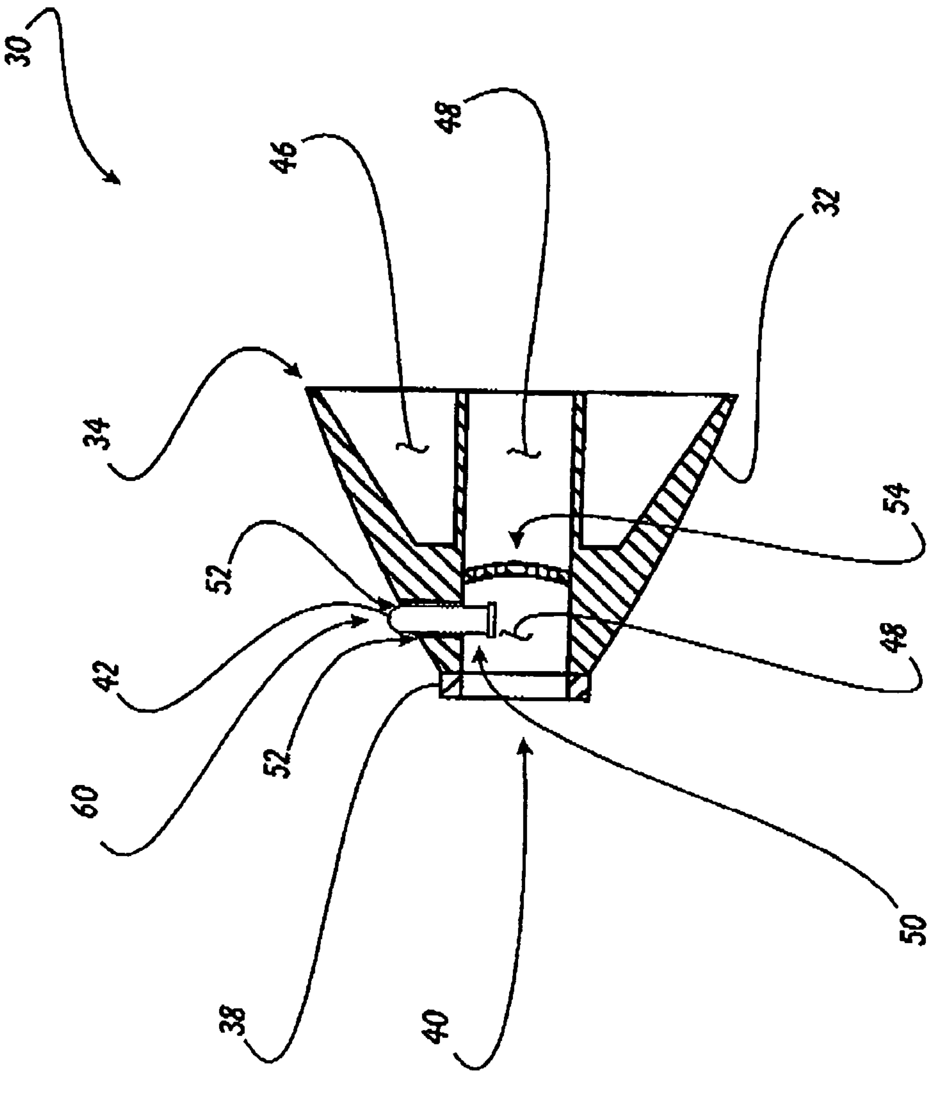
FIG. 5 is a cutaway side view of the attachment of FIGS. 2-4.

If the user first applies a collagen-enriched skin cream or lotion, and then passes the attachment 30 over that portion of skin, the stretching of the collagen fibers in the skin will actually make the skin absorb the lotion (and collagen enrichment) more fully and quickly. By driving the collagen enrichment into the skin, the fibers found within the skin are supplemented in a way that improves the skin tone above and beyond what was previously achievable through either manual rubbing in of the lotion, or through application of suction alone. FIG. 5 provides additional detail regarding the attachment of the present invention.

FIG. 5 is a cutaway side view of the attachment 30 of FIGS. 2-4. As can be seen, the housing 32 defines a suction bore 48 extending between the aperture 40 and the general vicinity of the skirt edge 34. At a point between the two ends, a screen 54 may be positioned to prevent contaminants from being sucked through the suction bare 48 and into the suction device (see FIG. 1). If the screen 54 is not included/attached within the bore 48, the suction developed at the aperture 40 will be greater than if it is in place. The sealing ring 38 is shown here a distinct element that is separate from the housing 32, however it should be understood that in some embodiments, the two elements may be combined into a single item.

The throttle 60 is a device used to adjustably narrow down or pinch off the suction bore 48 in order to create a variable suction force at the aperture 40. Unlike the prior pump regulating devices, the throttle acts on the suction side of the system, so that the throttle knob 42 can be positioned in close proximity to the tip of the attachment for convenient adjustment.

The throttle 60 is defined by the throttle knob 42, preferably extending outside of the outer wall of the housing 32. Somewhat adjacent to the throttle knob 42 is a threaded portion 52 of the throttle 60; the threaded portion 52 engages threads formed in the wall of the housing 32 in order to convert rotation into translation. The throttle 60 in this embodiment terminates in a plunger 50, which is extendable into the suction bore 48. In operation, the user can adjust the suction force created at the aperture 40 by rotating the throttle knob 42; rotation of the throttle knob 42 will cause the plunger 50 to travel into or out of the suction bore 48, thereby pinching off or opening up the suction bore diameter.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for delivering a medicinal formulation subcutaneously, comprising the steps of:

first applying a medicinal formulation to the surface of a person's skin in an application area;

applying an attachment to a suction-creating device, said attachment comprising:

a housing defined by a suction bore terminating at one end in a suction interface tube and at its other end in an aperture and defining an inner diameter, said inner diameter defined as the average inner diameter of said suction bore, said housing further comprising an annular ring void encircling said end of said suction bore and a throttle controllably extendable to protrude into said suction bore;

a suction-creating device defined by a head and a neck extending therefrom, said neck comprising a suction port stem extending therefrom and a ring encircling an outer rim of said neck in spaced relation with said suction port stem to form an annular ring between said outer rim and said suction port stem; and whereby said housing is attachable to said neck such that said suction port stem inserts into said suction bore and said outer rim inserts into said housing annular ring; and secondly applying a localized suction force to said skin surface in said application area with a suction-creating device.

2. The method of claim 1, wherein said attachment applying further comprises applying an attachment to a suction-creating device, wherein said outer wall is further defined by a tip diameter and a skirt edge diameter, said skirt edge diameter being larger than said tip diameter to said application area.

3. The method of claim 2, wherein said attachment applying further comprises applying an attachment to a suction-creating device, wherein said throttle is further defined by a throttle knob at one end, and terminating in a plunger at an opposing end, said plunger extending into said suction bore to said application area.

4. The method of claim 3, wherein said attachment applying further comprises applying an attachment to a suction-creating device, wherein said housing is further defined by an outer wall having a conical shape to said application area.

5. The method of claim 4, wherein said attachment applying further comprises applying an attachment to a suction-creating device, wherein said attachment is further defined by a sealing ring generally encircling said aperture to said application area.

6. The method of claim 5, wherein said attachment applying further comprises applying an attachment to a suction-creating device, wherein said outer wall adjacent to said skirt edge is cooperatively configured to encircle said neck when said suction port stem is inserted within said suction interface tube to said application area.

* * * * *